(12) United States Patent
Koppert

(10) Patent No.: US 6,686,517 B2
(45) Date of Patent: Feb. 3, 2004

(54) RAPHANUS WITH INCREASED ANTHOCYANIN LEVELS

(75) Inventor: Gerrit Koppert, Monster (NL)

(73) Assignee: Gain Harvest Development Ltd., Tai kok Tsui (HK)

(*) Notice: Subject to any disclaimer, the term of this patent is extended or adjusted under 35 U.S.C. 154(b) by 0 days.

(21) Appl. No.: 09/948,110

(22) Filed: Sep. 7, 2001

(65) Prior Publication Data

US 2003/0106109 A1 Jun. 5, 2003

(51) Int. Cl.$^7$ .............. C12N 5/02; A01H 1/00; A01H 1/02; A01H 5/00
(52) U.S. Cl. ............ 800/306; 800/260; 800/266; 800/268; 800/298; 435/410; 435/420
(58) Field of Search .................. 435/410, 420; 800/260, 266, 268, 298, 306

(56) References Cited

U.S. PATENT DOCUMENTS

| | | | |
|---|---|---|---|
| 3,643,376 A | * | 2/1972 | Poindexter et al. ............ 47/61 |
| 3,733,745 A | | 5/1973 | Ingerstedt et al. |
| 3,945,148 A | | 3/1976 | Oyama |
| 4,086,725 A | | 5/1978 | Li |
| 4,130,964 A | | 12/1978 | Caballero |
| 4,292,760 A | | 10/1981 | Krave |
| 4,642,939 A | | 2/1987 | Suzuki |
| 5,588,254 A | | 12/1996 | Adachi et al. |

FOREIGN PATENT DOCUMENTS

| | | |
|---|---|---|
| GB | 2 150 405 A | 7/1985 |
| GB | 2 163 634 A | 3/1986 |
| NL | 8901067 | 11/1990 |
| WO | WO 92/03146 A1 | 3/1992 |
| WO | WO 00/01222 A2 | 1/2000 |

OTHER PUBLICATIONS

Coogan et al. 2001. Pungency levels of white radish grwon in different seasons in Australia. Food Chemistry 72:1–3.*
Eshed et al. 1996. Less than additive epistatic interactions of quantitative trait loci in tomato. genetics 143:1807–1817.*
Giusti et al. 1996. Characterization of red radish anthocyanins. J. Food Sci. 61(2):322–326.*
Giusti et al. 1998. Anthocyanin pigment composition of red radish cultivars as potential food colorants. J. Food Sic. 63(2):219–224.*
Grill et al. 1969. Photocontrol of anthocyanin formation in turnip seedlings V. Differential responses to patterns of hypocotyls andd cotyledons. Planta 85:42–56.*
Hoshi et al. 1975. Genetical study on the formation of anthocyanins and flavanols in turnip varieties. Genetical studies on anthocyanins in Brassicaceae II. Bot. Mag. Tokyo 88:249–254.*
Khare et al. 1991. Chlorophyll/anthocyanin levels in radish cotyledons after treatment with GA3 and chloramphnicol. Indian J. Plant Physiol. 34:235–241.*

Kraft et al. 2000. Linkage disequilibrium and fingerprinting in sugar beet. Theor. Appl. Genet. 101:323–326.*
Park et al. 1993. Study on the anthocyanin pigment iin 'Comet' radish. Korean J. Food. Sci. 25(5):407–410.*
Sakamoto et al. 1998. Polymorphism of the s–locus glycoprotein gene (SLG) and the S–locus related gene (SLR1) in *Raphanus sativus* L. and self–incompatible ornamental plants in th Brassicaeae. Mol. Gen. Genet. 258:397–403.*
Savoskin et al. 1974. Effect of doubling the number of chromosomes on the qualitative composition and amount of anthocyanins in radish roots. Sov. Genet. 7(11):1393–1396.*
XP002191139, Database Biosis Online! Abstract for Lee Woo Sung et al., "Habitat Distribuation, Leaf Shape Variation And Folk Use Of Wild Radish In Korea," *Journal of the Korean Society for Horticultural Science*, vol. 36, No. 6, pp. 785–791 (1995).
XP002191140, Database Biosis Online! Abstract for Kaneko et al., "Induction Of Translocation In Radish By Gamma–Ray Irradiation Of Seeds In The Chromosome Addition Lines Of Radish With A Single Kale Chromosome", *Japanese Journal of Breeding*, vol. 42, No. 2, pp. 383–396 (1992).
XP002191141, Database Biosis Online! Abstract for Nozzolillo et al., "An investigation Of The Intracellular Site Of Anthocyanoplasts U\Sing Isolated Protoplasts And Vacuoles", *Plant Cell Reports*, vol. 7, No. 6, pp. 389–392 (1988).
XP002191142, Database Biosis Online! Abstract for Yasuda et al., "The Studies On The Spherical Bodies Containing Anthocyanins In Plant Cells I. Cytological And Cytochemical Observations On The Bodies Appearing In The Seedling Hypocotyls Of Radish Plants", *Cytologia*, vol. 50, No. 2, pp. 397–404 (1985).
XP002191143, Database Biosis Online! Abstract for Song Ji Young et al., "Expression of CHS, CHI, and DFR Genes in Response to Light in Small Radish Seedlings", *Journal of Plant Biology*, vol. 41, No. 4, pp. 277–282 (1998).

(List continued on next page.)

*Primary Examiner*—David T. Fox
*Assistant Examiner*—Medina A. Ibrahim
(74) *Attorney, Agent, or Firm*—Browdy and Neimark, P.L.L.C.

(57) ABSTRACT

The present invention relates to plants of the genus Raphanus containing increased levels of anthocyanins. In particular the edible sprouts and turnips of the Raphanus plants contain high levels of anthocyanins and thereby provide health-promoting effects. The anthocyanins in the Raphanus plants are present at a level of at least 100 nmol per gram of fresh weight and have an absorbance maximum at a wavelength in the range of 515 to 550 nm. The invention also provides methods for growing the Raphanus plants as purple sprouts, both in the form of alfalfa-type sprouts as well as in the form of two-leafed plantlets, referred to as cress or micro-vegetables. The invention further provides methods for producing anthocyanins based on growing the Raphanus plants and isolating anthocyanins therefrom.

14 Claims, 2 Drawing Sheets

OTHER PUBLICATIONS

XP002191135: "Black Radish", UPOV *Guidelines for the Conduct of Tests for Distinctness, Uniformity and Stability*, Geneva (Mar. 24, 1999).

XP002191136: Giusti et al., "Anthocyanin Pigment Composition of Red Radish Cultivars as Potential Food Colorants", *Journal of Food Science*, vol. 63, No. 2, pp. 219–224 (1998).

XP002191137, Advances In New Crops, Online!: Yamaguchi, "Asian Vegetables", (1990) retrieved from the Internet at URL:http://www.hort.purdue.edu/newcrop/proceedings1990/v1–387.html.

XP002191138: Giusti et al., "Elucidation Of The Structure And Conformation Of Red Radish (*Raphanus sativus*) Anthocyanins Using One– And Two–Dimensional Nuclear Magnetic Resonance Techniques", *J. Agric. Food Chem.*, vol. 46, pp. 4858–4863 (1998).

XP002191144, Database Biosis Online! Abstract for Makarova et al., "Inheritance Of Root And Leaf Characteristics In Radish Plants", *Genetika*, vol. 19, No. 2, pp. 304–311 (1983).

XP002191145, Database Biosis Online! Abstract for Moskova–Simeonova Dimka et al., "Effect of Urea Cytokin N–(2–chloro–4–pyridyl)–N'–phenylurea (4–PU–30) on Anthocyanin Accumulation in Some Plants", *Fiziologiya Na Rasteniyata(Sofia)*, vol. 18, No. 2, pp. 9–13 (1992).

European Patent Office: *Patent Abstracts of Japan*: Abstract for JP 02 265474, "Red Dye and Production of Floccose Tissue Containing Same", Nippon Shokubai Kagaku Kogyo Co Ltd (Oct. 30, 1990).

XP002191146, Database Biosis Online ! Abstract for Anh et al., "Production of Anthocyanin By Culture Of Hairy Roots Of *Raphanus–sativus* CV. Chungpihongsim", *Korean Journal of Botany*, vol. 35, No. 1, pp. 37–43 (1992).

European Patent Office: *Patent Abstracts of Japan*: Abstract for JP 01 086820, "Method for Cultivating 'Kaiware Daikon' and Apparatus Therefor", Miyachi Foods KK (Mar. 31, 1989).

XP002191147, Database Biosis Online! Abstract for Nasir et al., "Expression of Heterosis for Biochemical Traits in *Raphanus–sativus*", *Zeitschrift Fuer Acker– und Pflanzenbau*, vol. 155, No. 3, pp. 159–171 (1985).

XP002191168, Database Biosis Online! Abstract for Lichtenthaler et al., "Physiological Effects of Photosystem II Herbicides on the Development of the Photosynthetic Apparatus", *Photosynthesis Research*, vol. 1, No. 1, pp. 29–44 (1980).

XP002191172, Database WPI, Derwent Publications Ltd., Abstract for KR 9 504 772 B, "Antocyanin Prodn. From Callus of Radish . . . ", JIN RO Ltd, (May 10, 1995).

* cited by examiner

RAPHANUS WITH INCREASED ANTHOCYANIN LEVELS

FIELD OF THE INVENTION

The present invention relates to plants of the genus Raphanus that contain increased levels of anthocyanins, In particular the invention relates to edible Raphanus sprouts containing increased levels of anthocyanins, as well as to methods for their production.

BACKGROUND OF THE INVENTION

There is an increasing consumer demand for edible young vegetable plants, also referred to as sprouts. Sprouts may be produced by germinating seeds in either liquid medium and harvested before the cotyledons appear, as is e.g. done with alfalfa. Alternatively, seeds may be sown onto a water-soaked solid support, such as cellulose, and allowed to germinate and grow in e.g. small disposable containers until or beyond the cotyledons appear. Further growth of the plantlets may be arrested, e.g. by cooling the plantlets, usually before the plants reach a height of about 4 to 15 cm. The plantlets are then ready for consumption. Sprouts of e.g. cress, daikon (a type of radish sprout) and mustard grow this way are very popular and many other vegetables and herbs are nowadays also available in the form of sprouts. The popularity of vegetable sprouts may at least in part be explained by the notion that they are healthy. Sprouts are indeed known to be very rich in vitamins and minerals such as the vitamins C and B1, potassium, calcium, phosphorus, magnesium and iron, while at the same time they are low in calories. Daikon sprouts, i.e. Sprouts of *Raphanus sativa longipinatus*, are particularly popular in the U.S, and in Japan were they are usually sold as young two-leafed green plants. Unfortunately, daikon sprouts do not contain anthocyanins, a compound that could further contribute to the health promoting effect of these sprouts.

Anthocyanins are present in many plants of higher order where they are responsible for the red, violet, blue or bluish black colours of flowers and fits. They are heterocyclic 2-phenyl-chromenol multiring systems (see also Formula 1) of varying hydroxylation patterns and varying absorption spectra in the visible light range. The sugar-free aglycon components of anthocyanins are referred to as anthocyanidins. They are obtained easily by hydrolysis of the glycosides contained in common fruits.

More recently, anthocyanins have drawn attention for their health promoting effects (see e.g. WO 92/03146). E.g, it is known that anthocyanins can act as scavengers for oxygen radicals such as superoxide anion radical, hydrogen peroxide, hydroxyl radical, alkoxyl radicals, peroxyl radicals for singulett oxygen, and many other radicals. Anthocyanins have also been described as photobiological inhibitors that intervene as regulators and detoxifiers in sensitised photoreactions which take place through oxygen, thereby preventing the radical and radical chain reactions which damage cells and nucleic acids and protein molecules. Anthocyanins also protect against cell toxic and carcinogenic aldehydes such as e.g. 4-hydroxy-hexenal, 4-hydroxy-octenal, 4-hydroxy-nonenal, propanal, butanal, pentanal, hexanal, 2,4-hepta-dienal, malonic dialdehyde, and others. They even prevent the formation thereof within the framework of lipoperoxidative chain reactions. As such they may aid in the prevention of cancer or may delay the effects of ageing. Furthermore, they detoxify the acetaldehyde resulting from ethanol decomposition and the formaldehyde resulting from methanol decomposition.

Some species of Raphanus do produce anthocyanins, as is most notable from the red colour on the outside of the radish varieties as usually sold in Europe and the U.S. However, no Raphanus sprouts are available that contain appreciable levels of anthocyanins. Thus, it is an object of the present invention to provide for Raphanus plants containing increased levels of anthocyanins, in particular, it is an object of the present invention to provide for Raphanus plants, the sprouts of which contain increased levels of anthocyanins. Advantages of the anthocyanin containing sprouts of the invention over other consumable anthocyanin sources, such as e.g. fruits like blueberry or grapes, include (1) the much shorter cultivation time; (2) the relatively high concentration of anthocyanins in the sprouts allowing to consume only small amounts of the sprouts to meet a certain anthocyanin intake; and (3) the great variety a dishes and recipes in which the sprouts may be applied.

DESCRIPTION OF THE INVENTION

In a first aspect the invention relates to a plant of the genus Raphanus, whereby the plant upon germination of its seed produces a sprout that comprises one or more anthocyanins at a level of at least 100 nmol per gram fresh weight of sprout. A Raphanus sprout is herein defined as any developmental stage of a Raphanus plant ranging from a germinating seed to a plantlet that has a height of no more than 20, preferably no more than 17, 15, 14, 12 or 10 cm. Preferably, a Raphanus sprout is a Raphanus plant in a developmental stage beyond a germinating seed and preferably having no more than two leaves, i.e. the cotyledons. Further preferred embodiments of Raphanus sprout are herein defined below.

The Raphanus plants of the invention, or sprouts or turnips thereof, comprise anthocyanins at a level of preferably at least 100, 200, 400, 800, 1500, 3000, 4000, 5000 or 6000 nmol per gram of fresh weight plant material. Fresh plant material of the Raphanus plants of the invention has an anthocyanin content of preferably at least 100, 200, 400, 800, 1500, 2500, 3500 or 4500 ppm (parts per million). The anthocyanin levels or content may be determined photospectrometrically, using a malvine calibration curve to estimate the anthocyanin levels or contents of anthocyanins extracted from fresh plant material as described in Example 4. Preferably, these anthocyanin levels are present in sprouts of the Raphanus plants of the invention. It is to be understood that these anthocyanin levels relate to the total level of anthocyanins and thus may comprise the various glycosylation forms of the anthocyanins as well as anthocyanins with different anthocyanidin moieties as defined below. The anthocyanin levels are expressed per gram fresh weight of plant material, whereby preferably, if present, the roots have been removed by cutting prior to the determination of the fresh weight of the material to be extracted. Alternatively, the anthocyanin levels in the Raphanus plants of the invention may be defined by comparison to a reference plant of the invention such as the *Raphanus sativa* line V33, (i.e. ATCC No. PTA-3630). Thus, a Raphanus plants of the invention preferably has an anthocyanin content of preferably at least 2, 5, 10, 20, 50 or 75% of the anthocyanin content of the *Raphanus sativa* line V33, (i.e. ATCC No. PTA-3630), whereby tie anthocyanin content of both plants is determined in the same part(s) of the plants and/or at the same developmental stage of the plants and using tie same analytical technique.

The Raphanus plants of the invention comprise anthocyanins. Anthocyanin are herein defined as compounds having the following characteristics, (1) comprising a molecular structure as shown in Formula 1, having a 2-phenyl benzopyrylium cation (flavylium ion); (2) an intense red, pink, violet, or purple colour; (3) a strong shift in colour at high alkaline pH (towards green to yellow); (4) solubility in water. The anthocyanins contained in the Raphanus plants of the invention preferably comprise an anthocyanin having a anthocyanidin moiety with the structure of Formula 1, wherein $R_1$ is OH or $OCH_3$, and wherein $R_2$ is H, OH, or $OCH_3$. The anthocyanin may contain one or more glycosides attached to any of the hydroxyl groups of the anthocyanidin moiety, but not to each of the hydroxyl groups, whereby preferably at least the hydroxyl group in the 3 position is glycosylated. The Raphanus plants of the invention comprise anthocyanins that preferably have an absorbance maximum at a wavelength higher than 515, 520, 525, or 530 nm and preferably at wavelength less than 550, 545, 540 or 535 nm. The Raphanus plants of the invention preferably comprise anthocyanins that comprise an anthocyanin having an anthocyanidin moiety selected from the group consisting of cyanidin, peonidin, delphinidin, petunidin and malvidin, and more preferably the anthocyanins comprise an anthocyanin wherein the anthocyanidin moiety is malvidin.

The Raphanus plant of the invention preferably is a plant of the species *Raphanus sativa*, more preferably the plant is obtained through breeding and selection from the *Raphanus sativa* lines CGN 6924, CGN 7240, or both. Most preferably, the Raphanus plants of the invention are obtained through breeding and selection from the *Raphanus sativa* line V33, (i.e. ATCC No. PTA-3630).

Methods for breeding and selection of the Raphanus plants of the invention are well known to the skilled person. Generally such methods may include self- and cross-pollination and selection of new lines on the basis of colour, colour intensity, time of fading of (purple) colour to green, seed production, uniformity of germination time, height/length of the plant(let)s, absence of green descendants, taste, and size/shape of cotyledons. In order to intensify breeding, two generations may be grown per year, alternating growth in the Northern and Southern Hemisphere. In case interesting lines have not produced (sufficient) seed it may be necessary to maintain the line vegetatively in order to re-attempt seed production in the next season, This may require cutting of plants fully flowering. Several methods for cutting such plants are known in the art. A particularly advantageous method concerns cutting small shoots on the radish turnip together with some turnip tissue, treating it with cuttings-powder and incubating the slip under high humidity to grow roots.

In another aspect the invention relates to a Raphanus plant of the invention, wherein the plant is a sprout as herein defined above. In a preferred embodiment of the invention the sprout is a sprout prior to the two-leafed stage, i.e, so-called "alfalfa-type sprouts". Such sprouts may be cultured by methods and packaged in suitable containers for shipping and marketing as herein described below, The containers preferably contain a plurality of such sprouts wherein the sprouts are preferably ready for consumption.

In yet another aspect the invention relates to a Raphanus plant of the invention, wherein the plant is a plantlet that has at least two leaves. Preferably the plantlet has two leaves or no more than two leaves. The height or length of the plantlets, as measured from the root-tip to the top of the plantlet, is preferably at least 3, 4, or 5 cm and is preferably less than 20, 17, 15, 14, 12, 10, 8 or 6 cm. These plantlets/sprouts may be referred to as "cress-type sprouts" and are generally also referred to as micro-vegetables in the art. Such sprouts may be cultured by methods and packaged in suitable containers for shipping and marketing as herein described below. The containers preferably contain a plurality of such sprouts wherein the sprouts are preferably ready for consumption. Preferably the container contains at least 1, 2, 3, 4, 5, 6, or 8 plantlets per $cm^2$.

In a further aspect the invention relates to material from a Raphanus plant of the invention as herein defined above. The material may be a root, a stem, a stalk, a leaf, a petal, a siliqua, a seed, a turnip, pollen, meristem, callus, a sepal, a flower, a cell, tissue or a combination thereof. The material may suitably be used for various purposes, including breeding or culturing the Raphanus plants of the invention, as food or a food ingredient, as (part of) a pharmaceutical composition or for isolation of anthocyanins that may be used for various purposes as herein defined below.

The turnips of the Raphanus plants of the invention are characterised in that the anthocyanins are not (only) present in the skin but also in the turnip itself, which is in contrast to the usual red radish that is has a white core and where the anthocyanins are only present in its skin. Thus, in a further aspect the invention relates to a Raphanus plant that produces turnips containing anthocyanins within the tip itself, i.e. in the core of turnip and/or throughout the turnip. Preferably, the turnip may contain anthocyanins with an absorbance maximum at a wavelength higher than 500 or 505 nm and less than 520 or 515 nm or around 510 nm. The turnip may preferably contain anthocyanins with an absorbance maximum at a wavelength higher than 510 or 515 nm and less than 540 or 535 nm, or around between 520 and 530 nm. The anthocyanin content of the up is preferably as herein defined above.

In a further aspect the invention rein to methods for cultivating and/or producing the purple Raphanus sprouts of the invention. Preferably, such methods produce sprouts suitable for human (or animal) consumption, i.e. the sprouts are edible. A sprout is suitable for human consumption if it does not have non-edible substrate such as soil attached or clinging to it, Typically the sprouts are grown on a non-nutritive solid support, such as agar, paper towel, blotting paper, Vermiculite, Perlite, etc., with water and light supplied. A particularly preferred non-nutritive solid support for use in the method of the invention is cellulose which may be applied in the form of pads, sheets or particles such as e.g. described in Dutch Patent No. 1001570. Thus, if a sprout is not grown in soil, but on a solid support there is no need for it to be washed to remove non-edible soil. If a sprout is grown in a particulate solid support, such as soil, Vermiculite, Perlite, or cellulose, washing may be required to achieve a sprout suitable for human consumption.

The Raphanus sprouts of the invention are preferably grown in containers which are suitable for shipping and marketing, Typically such containers are plastic boxes or jars which contain a wetted pad at the bottom. The containers allow light to penetrate while providing a mechanically protective barrier. Numerous methods for the cultivation of sprouts are known, as exemplified by Dutch Patent No. 192969; U.S. Pat. Nos. 3,733,745; 3,643,376; 3,945,148; 4,130,964; 4,292,760 or 4,086,725; Steve Meyerowitz, In: "The Complete Guide to Sprouting, Sprouts The Miracle Food" Sproutman Publications, May 1998; James C. Schmidt, Horticulture Facts, "Growing Sprouts Indoors", (Rev. 4/81). The Raphanus sprouts of the instant invention can be stored and shipped in diverse types of containers such as jars, bags and boxes, open or closed, i.e. with or without lids, among many others. Any of the known methods for growing, packaging and shipping of sprouts are suitable.

Methods for producing Raphanus sprouts of the invention at least comprise the steps of (a) germinating seed of a Raphanus plant as herein defined above, in a suitable medium, under suitable conditions, and optionally in a container; and (b) growing the germinated seeds obtained in (a) under suitable conditions until a sprout of a desired developmental stage is obtained. The desired developmental stage may be a sprout prior to the appearance of the cotyledons, or may be a plantlet having at least two leaves and preferably no more than two leaves. A suitable growth medium preferably just contains water. Depending on the local quality of the tap-water further purification of the water may be required to demineralise the water and/or to remove chlorine, organic residues or other contaminants. The water is preferably free of microbial contaminants. Germination is preferably cared out at a temperature of 15–25° C., preferably at high humidity, most preferably a relative humidity of 100%. Germination may suitably be performed in a germination cell or room with controlled temperature and humidity.

A preferred embodiment of the invention concerns a method for producing Raphanus sprouts of the Alfalfa-type. The methods applied are essentially similar to those used for producing Alfalfa sprouts. Seeds are washed and/or soaked and placed in a rotating drum or container. Preferably this is done under climate controlled conditions with optimal (near 100%) humidity. The seeds rotate fast enough to avoid clinging of the seeds, yet slow enough to avoid damage to the germs. Germination may be performed with or without light and preferably at a temperature between 15 and 25° C. The temperature may be varied during the growth period. When the sprouts have grown to a desired stage, usually after about 100 hours (plus or minus 48 hours), they are harvested from the drum or container and may be washed with water. The sprouts may then be packaged into a variety of containers such as jars, bags and boxes in unit quantities ranging from 25 grams to bulk packing.

A further preferred embodiment of the invention concerns a method for producing Raphanus sprouts in the form of plantlets having at least two leaves and preferably no more than two leaves, i.e. preferably only having cotyledons and no true leaves. The method comprises the steps of (a) germinating seed of a Raphanus plant as defined herein above on a non-nutrative solid support (as described herein above) containing water and preferably no fertiliser or other additions, at a density of 3–12 seeds per cm$^2$, at a temperature of 10–35° C., preferably 15–25° C., at high humidity and, optionally in the dark; (b) growing the germinated seeds obtained in (a) at a temperature of at least 10° C. but no more than 35° C., preferably 15–25° C., at a humidity of at least 70% and under a daily cycle of light, until the germinated seeds have grown into plantlets having at least two leaves and a height of preferably at least 3, 4, or 5 cm; and optionally, (c) arresting further growth of the plantlets by cooling to a temperature between 1 and 6° C., more preferably the plantlets are cooled to a temperature between 1.5 and 4° C., most preferably to a temperature of about 2° C.

A further aspect of the invention relates to the (mass) production of seed for the purple Raphanus sprouts. Seed of a suitable Raphanus line producing purple sprout is sown in a field with suitable soil and a suitable climate, Seed is preferably sown in the months of October to May in the Northern Hemisphere or in the months of April to September in the Southern Hemisphere. Plants are grown and allowed to flower and pollinated with the help of insects, preferably bees. The plants are allowed grow further and to ripen with seeds. The plants are then preferably mown in a swath, after which they continue to ripen and are allowed to dry under the influence of wind and sun. A threshing machine is preferably used to harvest the seeds, which may be further selected on the basis of colour, shape and size, such that uniform batches of seed are obtained.

In a further aspect the invention relates to methods for producing anthocyanin, wherein the anthocyanin preferably is an anthocyanin as herein defined above. The method comprises the steps of (a) growing a Raphanus plant of the invention; (b) harvesting the Raphanus plant or a part thereof; (c) recovery of the anthocyanins in the plant or part thereof; and (d) optionally purification of the anthocyanins. The Raphanus plant to be applied in the method may be any Raphanus plant as herein defined. The entire Raphanus plant may be harvested, which may a sprout or a plantlet as herein defined above. Alternatively, anthocyanin-rich parts of the plants may be harvested such as e.g., the leaves or turnips of the plants. Recovery of the anthocyanin will usually comprise some form of grinding or homogenisation of the plant or parts thereof and may farther comprise extraction of the anthocyanins with water or preferably a diluted acid in water, such as e.g. 5% formic acid, or with organic solvents such as methanol, which may preferably also contain an acid, such as e.g. 5% formic acid. Methods for recovery and extraction of anthocyanins from plant materials are well known in the art and may likewise be applied to the Raphanus plants of the invention. The anthocyanins may be flier purified by e.g. chromatography as described in the Examples below (see also Fiorini, 1995, J. Chromatogr, 692: 213–219). The thus obtained anthocyanin preparations may be used for a variety of purposes, including e.g. their incorporation into foods or drinks, as a food ingredient, as a natural colouring agent or dye for food, drinks or other materials, as a (food or pharmaceutical grade) preservative, in particular for the preservation of oxidation sensitive compositions or they may be formulated in to food supplements or into pharmaceutical compositions in a manner known per se for anthocyanins from other sources, as e.g. described in WO 92/03146. Such pharmaceutical compositions may be used in the treatment of wounds, ulcers, inflammatory symptoms, and pathogenic conditions of the vascular system or of disturbances caused by a deterioration of the lipoid or glycide metabolisms. In addition, compositions comprising the anthocyanins of the invention may be used to improve (night) vision and/or treat tired eyes. Such compositions may further be used in the prevention of cancer and cardiovascular disease, and in reducing the effects of ageing, such as impaired memory. Likewise, the anthocyanin containing plants of the invention, or past thereof may be used as such for the above purposes.

The advantages of the invention include the plants, plantlets, sprouts and plant parts of the invention possessing health promoting effects as compared to the prior art Raphanus plants. These plants or parts thereof may thus be used as nutraceuticals or functional foods. A further advantage of these plants and part thereof is that they have an attractive colour that may be used to add a new decorative aspect to recipes and dishes. The plants of the invention may further advantageously be applied as source for anthocyanins, which may be isolated therefrom for a variety of purposes including active ingredients in pharmaceutical compositions, food ingredient and/or as natural dye. Finally, the plants of the invention have been obtained through classical breeding techniques from naturally occurring isolates. As such these plants are non-GMO, thereby greatly increasing the public acceptance of these plants or products therefrom.

EXAMPLES

Example 1

Figure 1:
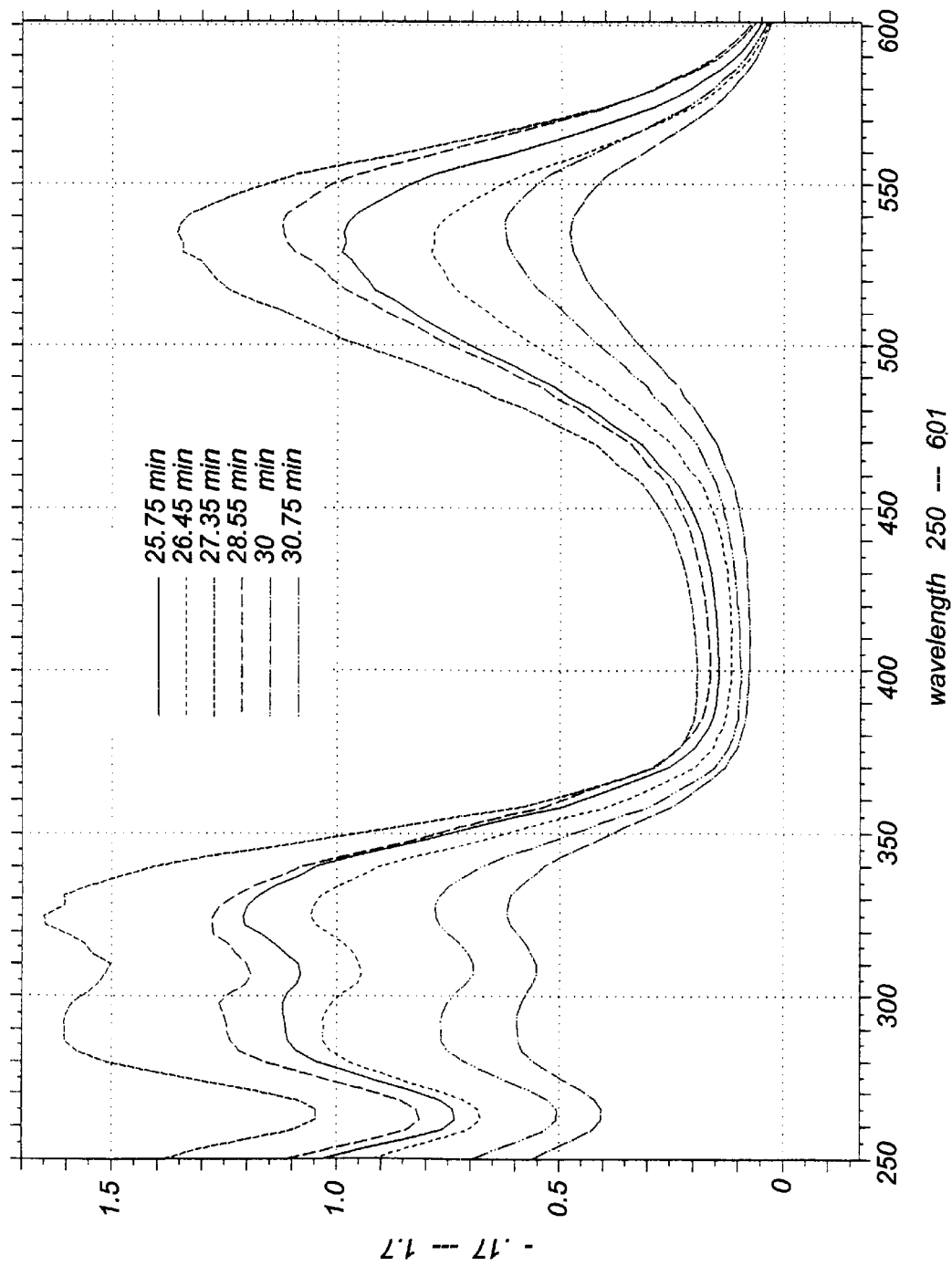
FIG. 1. Spectra of the anthocyanins as extracted from sprout of the *Raphanus sativa* line V33. The absorbance versus the wavelength is shown for each of the anthocyanins eluting from the HPLC at different times as indicated (see Example 4 for experimental details).

Breeding of Raphanus Lines Producing Purple Sprout

A total of 568 *Raphanus sativa* lines as available from public gene banks were screened for their capability to produce a purple sprout. 14 of those lines were found to produce a sprout with at least some purple colouring. After several generations of self-pollination and selection, most descendants did not produce a sufficiently intense purple colour. Only 2 out of the 14 lines produced a significantly intense purple colour and were selected for further breeding. These two lines, CGN 6924 and CGN 7240 were both obtained from the CGN gene bank at Plant Research International (formerly CPRO-DLO), Wageningen, The Netherlands and originated from the former German Democratic Republic and from China, respectively. Starting from these three lines a high frequency further breeding program was undertaken whereby two generations were grown per year, alternating growth in the Northern and Southern Hemisphere. Both self-pollination and crossing of lines were applied whereby new lines were selected on colour intensity, time of fading of purple colour to green, nicking time, seed production and amount of seeds per flower, height/length of the plant(let)s, uniformity of germination time, absence of green descendants, and size and shape of cotyledons. Generally it was found that the lines with purple colour showed reduced seed production. Per generation at least 200 combinations were screened. Several lines with very intense purple colour and that did not divide out green descendants were thus obtained. One such line, with designation V33 was deposited on Aug. 13, 2001 under the Budapest Treaty at the American Type Culture Collection, Manassas, Va., USA, and was assigned ATCC No. PTA-3630. This line may used as such for the production of sprouts or may be used in breeding programs, optionally in combination with CGN 6924 and CGN 7240, to cross the purple colour into conventional green varieties.

Example 2

Method for Producing Purple Raphanus Sprout in the Form of "Cress"

A method for producing Raphanus (daikon) sprout in the form of "cress" (Sakura Cress®) is described in Dutch Patent No. 192969. Basically, seed of a purple Raphanus line is placed in plastic containers (of e.g. 6×8 cm surface) having a water soaked solid support ("substrate") such as e.g. a sheet or pad of cellulose or fin peat on the bottom. A suitable substrate is described in Dutch Patent No. 1001570. The seeds are sown at a high density of about 3–6 seeds per $cm^2$. The containers wit the seeds are then allowed to germinate at 15–24° C. at high humidity (preferably a relative humidity of 100%). Germination may suitably be performed in the dark or with light and preferably is carried out in a germination cell or room with controlled temperature and humidity. After germination, which usually takes about 48 hours, the containers with seedlings are placed in a greenhouse where the temperature is kept at 15° C. or higher (preferably not higher than 25° C.) and humidity is preferably kept above 70% (relative humidity). The plantlets are then allowed to grow for another 48–72 hours until they reach a height of 5–14 cm and usually having no more than 2 leaves, i.e. the cotyledons. Additional light may be given to make the plantlets more sturdy. When the plantlets have reached the desired height or number of leaves, growth is arrested by cooling down to 2° C. The plantlets are further kept, stored and transported at this temperature, preferably until consumption.

Example 3

Method for Producing Purple Alfalfa-Type Raphanus Sprout

Seed of the V33 line is washed and soaked in water and placed in a slowly rotating drum at 15–25° C., under addition of a fine mist of water. This mist is provided every hour or differently according to the growing method and planning of the grower. The seeds slowly tumble in the drum, fast enough not to cling together and slow enough not to break the germs. After 100 hours with a variation of about 48 hours, the sprouts have developed into a red/purple shiny product, which is then washed and ready for packaging. The ratio of seed to harvestable product usually is 1:8 till 1:10, i.e. 1 kg seeds provides 8 to 10 kg of sprouts. Additional lighting may be added during the germination resulting in a more intense purple colour.

Example 4

Method for Analysis of Anthocyanin Levels and Anthocyanidin Structures in Purple Raphanus Sprout Methods
Materials The following materials were analysed:

Two-leafed daikon sprout plantlets of the *Raphanus sativa* line V33. This material was cultured as described in Example 2 and was cut just above the roots and immediately frozen in liquid nitrogen.

Turnips from a full-grown plant of the *Raphanus sativa* line V33, The turnips were rinsed with water, cut into small pieces (which showed nice purple coloured patterns) and frozen in liquid nitrogen.

Two-leafed daikon sprout plantlets of the *Raphanus sativa* variety "Mino White" were cultured and treated as described for the V33 sprouts.

Two-leafed radish sprout plantlets of the *Raphanus sativa* variety "Recipar" (obtainable from Novartis) were cultured and treated as described for the V33 sprouts.

Two-leafed sprout plantlets of a Broccoli variety were cultured and treated as described for the V33 sprouts.

Two-leafed daikon sprout plantlets of the *Raphanus sativa* line CGN 6924 (starting cultivar) were cultured and treated-as described for the V33 sprouts.

Radish turnips of the Raphanus sativa variety "Hoogvliet" were obtained in a Dutch supermarket. The red skins were peeled from the turnips, cut into small pieces and frozen in liquid nitrogen.

Frozen Materials were Stored at −80° Until Extraction.
Extraction

Before extraction tie materials were ground to a fine powder in a Waring blender that was pre-cooled with liquid nitrogen. The ground materials were treated with a 5-fold excess (volume in ml per weight in grams) of dichloromethane for removal of lipophilic substances such as chlorophyl. After filtration of dichloromethane, the material was extracted overnight in the dark in a 5-fold excess (volume in ml per weight in grams) of a 5% formic acid solution in water. The non-dissolved materials were removed by centrifugation after which the coloured supernatant was filtered. The filtrate was stored at 4° C. in the dark.

Purification

Part of the crude extracts were purified by solid-phase extraction on $C_{18}$-columns (Supelco DSC18, 2 g per column). After solvatation of the column with methanol and equilibration with 5% formic acid, approximately 22.5 ml extract was applied per column (in total 100 ml per sprout material, 150 ml per turnip extract) and washed with at least 3 column volumes 5% formic acid, 1×1N HCl and 1×0.2% HCl. The coloured substances were then fluted from the columns using 1 column volume 0.1% HCl in methanol. Methanol was removed from the collected solutions using a Büchi rotavapor and the residues were freeze-dried after dilution with water.

Analysis

The freeze-dried extracts thus obtained were weighed to determine the yields The extracts were analysed using a Waters HPLC system with a photodiodearray-detection system, such that spectra were obtained for all the compounds in the extract. In addition, the anthocyanin compounds in the extracts were quantified using a calibration curve based on malvine (malvidine-(3,5)-diglucoside). The latter compound is probably the basis of one or more of the anthocyanins in the purple Raphanus plant materials. The applied system consisted of a 150×4.6 (internal diameter) mm Luna 3 µm reversed phase-($C_{18}$-) column, using a flow of 0.75 ml/min. with an eluens consisting of a 35 to 55% methanol gradient in 5% formic acid.

Results

Colours

Most of the plant materials analysed exhibited some degree of purple colour, except for the Mino White sprout. This degree of purple colour was reflected in the extracts: the extract of Mino White was completely without any purple colour, the Recipar-extract only had some violet colour, the extract of the CGN 6924 starting cultivar and the broccoli-extract were slightly more purple and the V33 extracts showed an intense purple colour.

Extract Yields

The yields for the extracts were as follows:

| Broccoli | 36.8 mg | 0.19% |
| Mino White | 51.0 mg | 0.25% |
| V33 sprouts | 236.4 mg | 0.78% |
| CGN 6924 cultivar | 47.2 mg | 0.24% |
| Recipar | 30.9 mg | 0.19% |
| V33 turnips | 52.2 mg | 0.16% |

These yields relate to the total weights of the extracts over the total weights of the extracted plant materials. By comparing the yield of the V33 sprouts with those of the Raphanus sprouts that contain no or very little anthocyanins it can be estimated that the yield of extracted anthocyanins from the V33 sprouts is about 195 mg, or about 0.64%.

Spectra of the Extracted Compounds

All extracts show a large number of absorbance peaks in the chromatograms at 254 and 340 nm. For the most part these compounds are not anthocyanins but other compounds that were extracted and co-purified with the anthocyanins. Characteristic for the anthocyanins is an absorbance at 510–540 nm.

Broccoli

Only a few anthocyanin peaks are visible. The most prominent eluted at a retention time of 25.93 min and has an absorbance maximum at 325 nm and at 535–540 nm. Based on the coinciding retention times and spectra these anthocyanins could be the same or could be very similar to the anthocyanins found in the V33 materials (see below).

Mino White

No anthocyanin peals were found in the Mino White extract, as was expected in view of the absence of any purple colour in the extract.

V33 Sprouts

A number of anthocyanin peaks were visible, mostly eluting with a retention time in the range of 23–31 min. The spectra of these anthocyanins show absorbance maxima at 325–330 mn and at 530–535 nm (see FIG. 1).

CGN 6924 Cultivar

Figure 2:
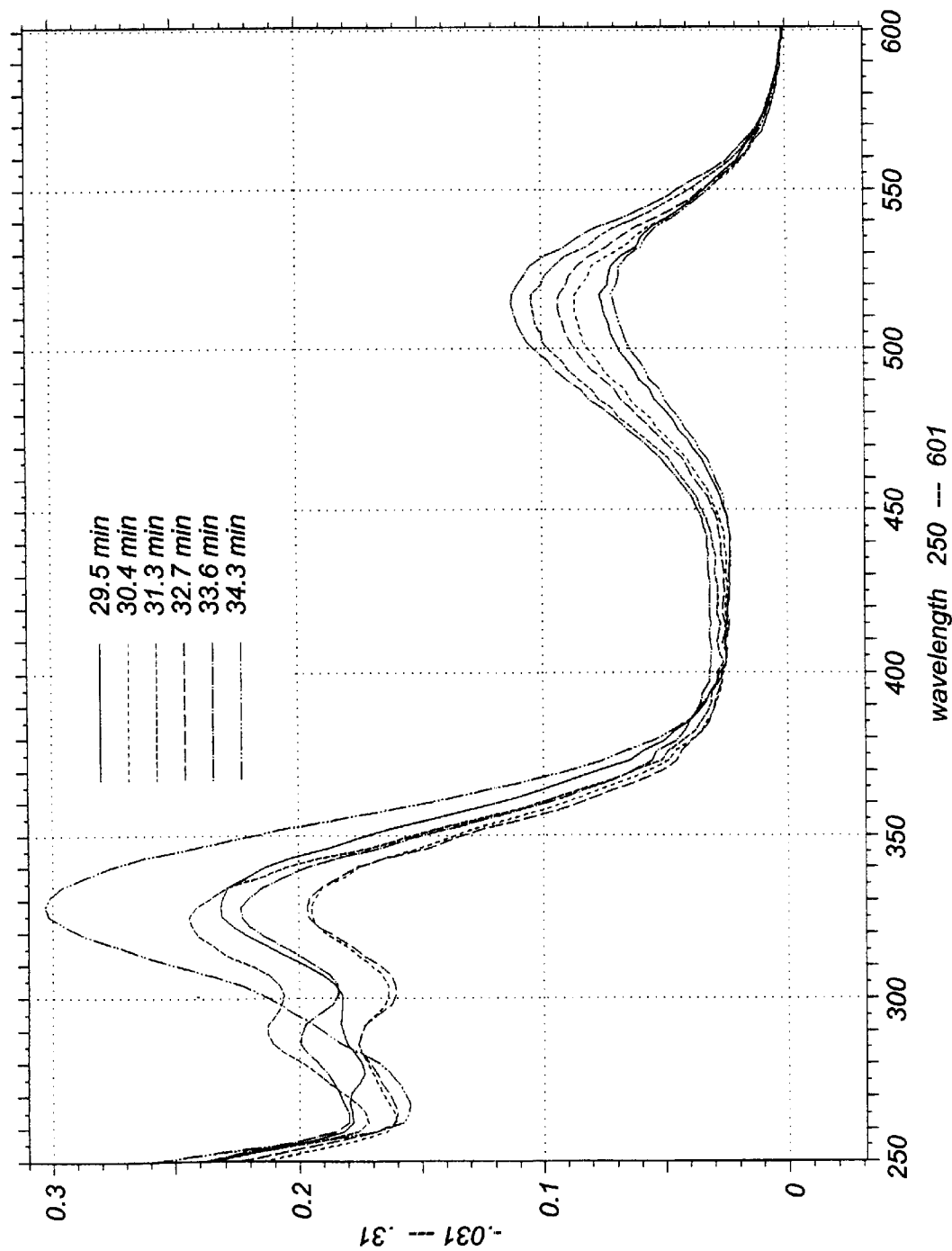
FIG. 2. Spectra of the anthocyanins as extracted from sprout of the *Raphanus sativa* line CGN 6924 (starting cultivar). The absorbance versus the wavelength is shown for each of the anthocyanins eluting from the HPLC at different times as indicated (see Example 4 for experimental details).

Despite a number of similarities in the pattern as compared with that of tie V33 extract, the CGN 6924 chromatogram (FIG. 2) clearly differs from the V33 chromatogram in the presence of a number of peaks (not anthocyanins) with an absorbance in the UV-range and eluting 40–47 min (see FIG. 2 at 254 en 340 nm). Anthocyanins are present in the CGN 6924 material but only in small amounts (see FIG. 2 at 510 nm). The anthocyanins in the CGN 6924 line clearly differ from the anthocyanin in the V33 line by having an absorbance maximum at 515 nm instead of a maximum in the range of 530–535 nm. A relatively high extinction is also found at 325 and at 285 nm, with the strongest extinction at 325 nm. However it cannot be exclude that other, non-anthocyanin compounds co-elute that influence the extinction in this area.

Recipar

Only minute amounts of anthocyanins were found in Recipar, showing absorbance maximum at 530–535 nm and at 325–330 nm. These anthocyanin therefore appear to be similar to those found in the V33 line. Also the retention times of these anthocyanins are very similar, however, there is a huge quantitative difference.

V33 Radish Turnips

The V33 turnips contain large quantities of anthocyanins. However, in contrast to the usual red radish the anthocyanins are not present in the skin but rather in the turnip itself. The spectra of these anthocyanins are interesting as they show two types of anthocyanins: one with an absorbance maximum at approximately 510 nm and one with a maximum at 520–530 nm. The colour of the extract is therefore also in between the colours of the extracts of the red radish skins and of the V33 sprouts. The other maxima have normal values of 285 and 325–330 nm. The anthocyanins with a maximum at 520–530 nm elute in the same area as those found in the V33 sprouts, indicating that these are probably the same compounds. However, clearly also different anthocyanins are present in this extract as is evident from the absorbance at 510 nm.

Red Radish Skins of the "Hoogvliet" Variety

The anthocyanins found in the skins of the red radish turnips of the "Hoogvliet" variety clearly differ from those found in the V33 sprouts by having an absorbance maximum at 508–510 nm and a clearly higher extinction at 285 nm as compared to that at 325 nm.

Quantification

A calibration curve was made using increasing concentrations of commercially available malvine chloride. This curve was used to estimate the quantities of anthocyanins per extract and also per amount of plant material. Table 1 shows the estimated quantities of anthocyanin expressed in nmol per μgram extract and in nmol per gram plant material, respectively. Table 2 shows the estimated quantities of anthocyanin content of the extracts and of the plant materials, respectively.

TABLE 1

Estimated quantities of anthocyanin expressed in
nmol per μgram extract and in nmol per gram plant material

|  | content in extract (nmol/μg) | content in plant (nmol/g) |
|---|---|---|
| Broccoli | 0.063 | 122 |
| Mino White | 0.000 | 0 |
| V33 sprouts | 0.892 | 6925 |
| CGN 6924 sprouts | 0.034 | 79 |
| Recipar sprouts | 0.024 | 39 |
| V33 turnips | 0.822 | 1293 |
| Red radish skins | not determined | not determined |

TABLE 2

Estimated quantities of anthocyanin content
of the extracts and of the plant materials.

|  | anthocyanin content of the extracts (%) | anthocyanin content of the plant materials (ppm) |
|---|---|---|
| Broccoli | 4.4 | 84 |
| Mino White | 0.0 | 0 |
| V33 sprouts | 61.6 | 4785 |
| CGN 6924 sprouts | 2.3 | 55 |
| Recipar sprouts | 1.7 | 27 |
| V33 turnips | 56.8 | 894 |
| Red radish skins | not determined | not determined | ppm = parts per million,
1 ppm = 0.0001%

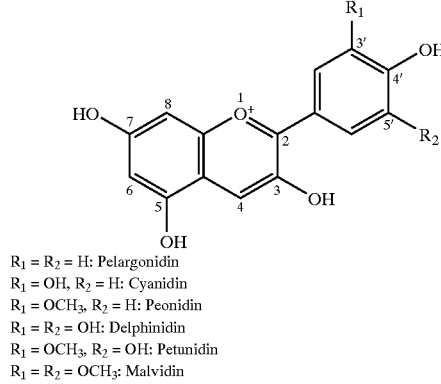

Formula 1

$R_1 = R_2 = H$: Pelargonidin
$R_1 = OH, R_2 = H$: Cyanidin
$R_1 = OCH_3, R_2 = H$: Peonidin
$R_1 = R_2 = OH$: Delphinidin
$R_1 = OCH_3, R_2 = OH$: Petunidin
$R_1 = R_2 = OCH_3$: Malvidin

What is claimed is:

1. A plant of the genus Raphanus, whereby the plant, upon growth of its germinated seed in a medium that comprises water, at a temperature of 10–35° C. under high humidity and under a daily cycle of light, produces a sprout that comprises anthocyanins at a level of at least 100 nmol per gram fresh water of sprout, wherein the plant is *Raphanus sativa* line V33 (ATCC No. PTA-3630).

2. The plant of claim 1, wherein the anthocyanins have an absorbance maximum in the range of 515–550 nm.

3. A plant according to claim 1, wherein the plant is a sprout.

4. A plant according to claim 1, wherein the plant is a sprout prior to the two-leafed stage.

5. A container containing a plurality of sprouts according to claim 3.

6. A plant according to claim 1, wherein the plant is a plantlet that has at least two leaves and a height of less than 20 cm.

7. A plant according to claim 1, wherein the plant is a plantlet that has two leaves.

8. A container containing a plurality of plantlets as defined in claim 6 or 7.

9. A container according to claim 8, wherein the container contains at least 3 plantlets per cm².

10. Material from a plant according to claim 1, wherein the material is a root, a stem, a stalk, a leaf, a petal, a siliqua, a seed, a turnip, pollen, meristem, callus, a sepal, a flower, a cell, tissue or a combination thereof.

11. A method for producing sprout as defined in claim 3, wherein the method comprises the steps of:

(a) germinating seed of said Raphanus plant, in a medium comprising water and at a temperature of 10–35° C., under high humidity, optionally in a container, wherein the Raphanus plant is as defined in claim 1 or 2;

(b) growing the germinated seeds obtained in (a) on a non-nutritive solid support soaked in a medium comprising water, at a temperature of 10–35° C., under high humidity and under a daily cycle of light, until a sprout of a desired developmental stage is obtained.

12. A method for according to claim 11, wherein the seeds are germinated in (a) in a rotating drum or container while spraying the seed with water at least once, and optionally with the addition of light, and wherein the germinated seeds obtained in (a) are grown under the conditions defined in (b) for at least 48 hours.

13. A method according to claim 11, wherein in (a) the seeds are germinated on the non-nutritive solid support at a density of 3–12 seeds per cm², and wherein in (b) the germinated seeds obtained in (a) are grown into plantlets having at least two leaves; and wherein an optional step (c) further growth of the plantlets is arrested by cooling to a temperature between 1 and 6° C.

14. A method for producing anthocyanin, wherein the method comprises the steps of:

(a) growing said Raphanus plant as defined in claim 1 or 2;

(b) harvesting the Raphanus plant or a part thereof;

(c) recovery of the anthocyanins in the plant or part thereof; and (d) optionally, purifying the anthocyanins.

* * * * *